(12) United States Patent
Banks et al.

(10) Patent No.: US 7,458,989 B2
(45) Date of Patent: Dec. 2, 2008

(54) INTRAOPERATIVE JOINT FORCE MEASURING DEVICE, SYSTEM AND METHOD

(75) Inventors: Scott A. Banks, Gainesville, FL (US); Hiromasa Tanino, Asahikawa (JP)

(73) Assignee: University of Florida Rearch Foundation, Inc., Gainesville, FL (US)

( * ) Notice: Subject to any disclaimer, the term of this patent is extended or adjusted under 35 U.S.C. 154(b) by 379 days.

(21) Appl. No.: 11/172,556

(22) Filed: Jun. 30, 2005

(65) Prior Publication Data

US 2007/0005145 A1 Jan. 4, 2007

(51) Int. Cl.
*A61F 2/32* (2006.01)
*A61F 2/36* (2006.01)
*A61B 5/00* (2006.01)
*A61B 5/103* (2006.01)

(52) U.S. Cl. .................. 623/22.45; 623/23.42; 600/300; 600/587

(58) Field of Classification Search ............... 623/22.41, 623/22.45, 20.15, 22.42–23.11, 23.39, 18.12, 623/22.4, 22.11, 22.12, 23.4, 23.42; 606/102
See application file for complete search history.

(56) References Cited

U.S. PATENT DOCUMENTS

| | | | |
|---|---|---|---|
| 4,841,975 A | 6/1989 | Woolson | |
| 5,362,311 A | 11/1994 | Amino et al. | |
| 5,413,610 A | 5/1995 | Amino et al. | |
| 5,725,592 A | 3/1998 | White et al. | |
| 5,769,092 A | 6/1998 | Williamson, Jr. | |
| 5,880,976 A | 3/1999 | DiGioia, III et al. | |
| 5,902,340 A | 5/1999 | White et al. | |
| 5,995,738 A | 11/1999 | DiGioia, III et al. | |
| 6,002,859 A | 12/1999 | DiGioia, III et al. | |

(Continued)

FOREIGN PATENT DOCUMENTS

DE 10151438 1/2003

(Continued)

OTHER PUBLICATIONS

Corie Lok, Hip Checker for Easier Surgery, Technology Review, Feb. 2004, p. 28, vol. 107, No. 1.

(Continued)

*Primary Examiner*—Bruce E. Snow
*Assistant Examiner*—Megan Wolf
(74) *Attorney, Agent, or Firm*—Akerman Senterfitt; Gregory A. Nelson; Peter A. Chiabotti

(57) ABSTRACT

A surgical device for joint replacement surgery includes an intraoperative joint head having a stem attachment structure where the stem attachment structure may be removably attachable to a stem and a force sensor housed by the joint head for measuring in vivo forces during surgery. The in vivo forces may be generated by one or more of tension provided by soft tissue, load application during surgery, limb movement during surgery, and a combination thereof. Also, the joint head may provide a cavity where the stem attachment structure houses the force sensor and may be removably insertable in the joint head cavity. A method of performing joint replacement surgery includes installing an intraoperative joint head having a force sensor housed by the joint head and a stem attachment structure, the stem attachment structure being removably attachable to a stem, measuring joint forces, and adjusting an implant parameter based on the measured joint forces.

19 Claims, 8 Drawing Sheets

U.S. PATENT DOCUMENTS

| | | | |
|---|---|---|---|
| 6,447,448 | B1 | 9/2002 | Ishikawa et al. |
| 6,583,630 | B2 | 6/2003 | Mendes et al. |
| 6,610,096 | B2 | 8/2003 | MacDonald |
| 6,702,821 | B2 | 3/2004 | Bonutti |
| 6,711,431 | B2 | 3/2004 | Sarin et al. |
| 6,746,487 | B2 * | 6/2004 | Scifert et al. ............ 623/22.12 |
| 6,810,753 | B2 | 11/2004 | Valdevit et al. |
| 6,821,299 | B2 | 11/2004 | Kirking et al. |
| 2001/0021876 | A1 | 9/2001 | Terrill-Grisoni et al. |
| 2002/0077540 | A1 | 6/2002 | Kienzle |
| 2003/0153829 | A1 | 8/2003 | Sarin et al. |
| 2003/0181987 | A1 * | 9/2003 | Muirhead-Allwood ... 623/22.15 |
| 2004/0097952 | A1 | 5/2004 | Sarin et al. |
| 2004/0102792 | A1 | 5/2004 | Sarin et al. |
| 2004/0117026 | A1 | 6/2004 | Tuma et al. |
| 2004/0230199 | A1 | 11/2004 | Jansen et al. |
| 2004/0254584 | A1 | 12/2004 | Sarin et al. |
| 2005/0143828 | A1 * | 6/2005 | Collins et al. ............ 623/18.11 |
| 2005/0203384 | A1 | 9/2005 | Sati et al. |
| 2006/0095047 | A1 * | 5/2006 | de la Barrera ............... 606/102 |

FOREIGN PATENT DOCUMENTS

| | | |
|---|---|---|
| FR | 2 689 390 | 10/1993 |
| GB | 1293844 | 10/1972 |
| GB | 2382777 | 6/2003 |
| WO | 97/30652 | 8/1997 |
| WO | 2004001569 | 12/2003 |
| WO | 2004014219 | 2/2004 |
| WO | 2004030556 | 4/2004 |

OTHER PUBLICATIONS

P. Peters, F. Langlotz, L.-P. Nolte, Computer assisted screw insertion into real 3D rapid prototyping pelvis models, Clinical Biomechanics, 2002, pp. 376-382, vol. 17, No. 5.

Steve Cohan, Robodoc achieves pinless registration, Industrial Robot: An International Journal, Oct. 2001 vol. 28 Issue: 5 p. 381-386.

Yasuhiro Kawasaki, Fumihiko Ino, Yasuharu Mizutani, Noriyuki Fujimoto, Toshihiko Sasama, Yoshinobu Sato, Nobuhiko Sugano, Shinichi Tamura, and Kenichi Hagihara, High-Performance Computing Service Over the Internet for Intraoperative Image Processing, IEEE Transactions On Information Technology In Biomedicine, Mar. 2004, pp. 36-46, vol. 8, No. 1.

D D Frantz, A D Wiles, S E Leis and S R Kirsch, Accuracy assessment protocols for electromagnetic tracking systems, Physics In Medicine And Biology, 2003, pp. 2241-2251, vol. 48, No. 14.

Dong-Soo Kwon, Yong-San Yoon, Jung-Ju Lee, Seong-Young Ko, Kwan-Hoe Huh, Jong-Ha Chung, Young-Bae-Park, Chung-Hee Won, Arthrobot : A New Surgical Robot System for Total Hip Arthroplasty, 2001, pp. 1123-1128, vol. 2.

Mark N. Charles, MD, Robert B. Bourne, MD, J. Roderick Davey, MD, A. Seth Greenwald, MD, Bernard F. Morrey, MD, and Cecil H. Rorabeck, MD, Soft-Tissue Balancing of the Hip, The Role Of Femoral Offset Restoration, The Journal Of Bone & Joint Surgery, May 2004, vol. 86-A, No. 5, pp. 1078-1088.

Donald Longjohn, MD, and Lawrence D. Dorr, MD, Brief Communication: Soft Tissue Balance of the Hip, The Journal of Arthroplasty, 1998, vol. 13 No. 1, pp. 97-100.

Ofer Ron, B.A., Leo Joskowicz, Ph.D., Charles Milgrom, M.D., and Ariel Simkin, Ph.D., Computer-Based Periaxial Rotation Measurement for Aligning Fractured Femur Fragments from CT: A Feasibility Study, Computer Aided Surgery, 2002, vol. 7, pp. 332-341.

Robert B. Bourne, MD, FRCSC, and Cecil H. Rorabeck, MD, FRCSC, Soft Tissue Balancing The Hip, The Journal of Arthroplasty, 2002, vol. 17, No. 4, Suppl. 1, pp. 17-22.

Otto Müllera,, Wolfgang J. Parakb, Markus G. Wiedemanna, Franz Martinia, Three-dimensional measurements of the pressure distribution in artificial joints with a capacitive sensor array, Journal of Biomechanics, 2004, vol. 37, pp. 1623-1625.

* cited by examiner

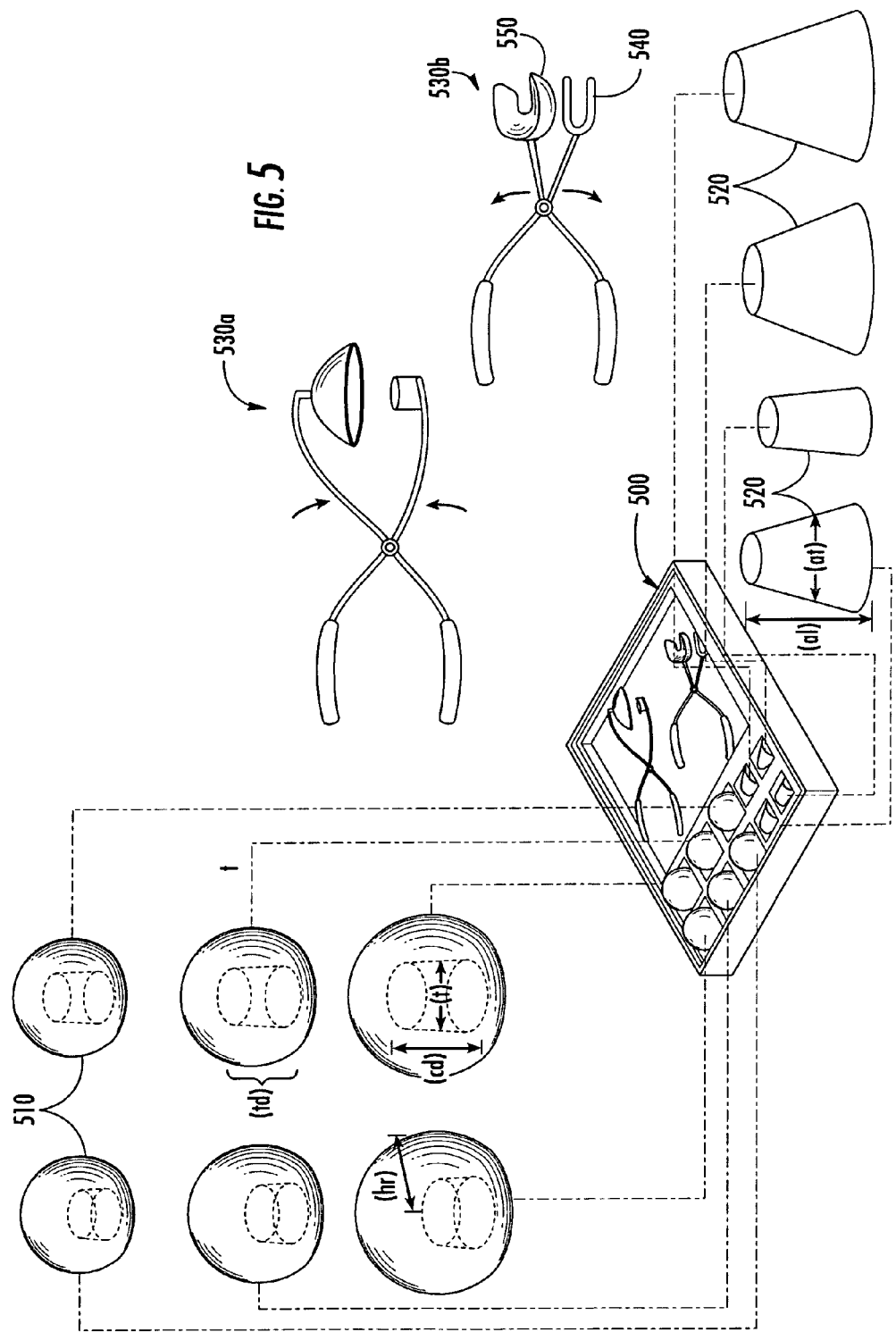

INTRAOPERATIVE JOINT FORCE MEASURING DEVICE, SYSTEM AND METHOD

CROSS-REFERENCE TO RELATED APPLICATIONS

Not applicable.

FIELD OF THE INVENTION

The present invention relates to surgical systems, devices and methods, and more particularly, to surgical systems for measuring joint loads during surgery.

BACKGROUND OF THE INVENTION

Joints are maintained in a secure position in the body via tension provided by soft tissues, such as muscles, tendons, and ligaments. For example, one soft tissue that secures the hip joint is the abductor muscle. The abductor muscle attaches to the pelvic bone at one end and to the femur on the other end and is tensed. In the event of surgery affecting the joint, soft tissue tension is often affected; however, optimal soft tissue tension is not always returned to patient.

Total hip replacement or arthroplasty ("THA") operations have become increasingly common in the United States, with more than 200,000 such operations occurring annually. A THA procedure can replace portions of the femur and the acetabulum with implants. More particularly, during a THA operation, the femoral head can be removed. The removal of the femoral head allows the two points of attachment of the abductor muscle to come together and results in a loss of tension in the abductor muscle. When a surgeon implants a femoral prosthetic, the two points of attachment are moved and result in the return of soft tissue tension. The size and the arrangement of the prosthetic can determine the amount of soft tissue tension returned to the joint. Especially, osteoarthritis secondary to developmental dysplasia of the hip can present numerous technical challenges to a THA procedure, including altered femoral anatomy, limb length discrepancy, and soft tissue contractures.

After the procedure, problems can arise with implants, including aseptic loosening, polyethylene wear, and dislocation. Dislocation after THA can cause discomfort, inconvenience and expense. The incidence of dislocation is related to many factors; the orientation of the hip replacement implants, implant geometry, patient related factors, and improper soft tissue tensioning, or even soft tissue laxity. Despite much research regarding dislocation after THA, the incidence of dislocation has not significantly declined.

Despite the occurrence of post-surgical dislocation, or even post-surgical discomfort, doctors have routinely relied upon measurements obtained by implanting devices within the deceased. For instance, instruments and devices have been constructed and arranged to be used in deceased test subjects for measuring forces at the hip and/or the implant. Still further, it is not uncommon for the particular body components to be removed and isolated for the application of static loads.

Devices created for such testing do not consider or take into effect the combined stresses experienced by the hip components during life. For instance, a typical testing situation may apply a load at only one particular point of an implant and only at one particular angle. The devices used in such research are not capable of measuring forces from a variety of different load applications, as truly experienced by the hip of an ambulatory person or even the soft tissue tension through a complete range of motion. Importantly, such devices, and the testing situations in which they are arranged, are not designed to take into account the effects and properties of live soft tissues, which have significantly different elastic properties in comparison to dead soft tissues. Finally, these devices and the artificial testing situations in which they are used to develop models, cannot possibly take into account the unique anatomical considerations presented by the individual patient.

Further, intraoperative procedures for measuring forces experienced by the implant and at the hip are non-existent because devices for measuring such forces do not exist. Instead of quantitatively determining the forces experienced by a hip implant that is implanted in the actual patient, a doctor may perform a series of manual tests while observing the hip. The doctor may then use subjective judgment to determine what the doctor believes to be the best arrangement.

Accordingly, devices, systems, and methods designed for obtaining quantitative intraoperative measurements are needed for determining the proper placement and arrangement of an implant specific to the unique anatomy of each particular patient. The devices, systems, and methods will provide quantitative intraoperative measurements that allow the surgeon to select implant size, placement and arrangement that will result in an optimal tension provided by the soft tissues.

SUMMARY

The present invention provides an intraoperative device, kit, method and system for measuring joint forces, such as soft tissue tension, experienced by implants so that surgeons can quantify needed adjustments for implants and prosthetics. With the device, kit, method and system, surgeons can measure joint forces intraoperatively, make adjustments based on measurements instead of subjective observation as was done in the prior art, and provide optimal implant placement and size. Further, providing multiple intraoperative components that are removably attachable allows for components of various dimensions to be tested without subjecting the patient to potentially damaging implanting, such as seating multiple femoral implants by hammering them into the femoral cavity and risking femoral cavity injury, and removing of multiple test components that are integrated and do not provide attachable and detachable components.

A surgical device for joint replacement surgery can include an intraoperative joint head having a stem attachment structure where the stem attachment structure can be removably attachable to a stem. The device can also include a force sensor housed by the joint head for measuring in vivo forces during surgery. The in vivo forces can be generated from one or more of tension provided by soft tissue, load application during surgery, limb movement during surgery, and a combination thereof. The joint head can provide a cavity and the stem attachment structure can house the force sensor and can be removably insertable in the joint head cavity.

In one embodiment, the joint head can be at least partially spherically shaped. For instance, the joint head can be shaped as an anatomical structure such as one or more of a femoral head, a humeral head, or any other suitable anatomical structure. Additionally, the stem can be the implant and the joint head can be a trial joint head dimensioned as an implant for measuring in vivo forces during surgery. The stem attachment structure can include a recess for receiving insertion of the stem. Also, the force sensor can be located at one or more positions such as along an axis of the stem, offset from the axis of the stem, and a combination thereof. The force sensor can be a strain sensor.

Also in accordance with the inventive aspects, a kit for assisting joint replacement procedures is provided. The kit can include an intraoperative joint head having a stem attachment structure where the stem attachment structure can be removably attachable to a stem. The device can also include a force sensor housed by the joint head for measuring in vivo forces during surgery. The in vivo forces can be generated from one or more of tension provided by soft tissue, load application during surgery, limb movement during surgery, and a combination thereof. The kit can also provide an intraoperative joint head tool, such as an assembly or disassembly tool.

In one arrangement, the kit can include one or more series of joint heads where each joint head can provide at least one unique dimension relative to the joint heads in the series. The dimension can be one or more of joint head radius, joint head cavity depth, cavity taper, trunion dimension and a combination thereof or any other relevant dimension. In such an arrangement, the cavity taper and/or trunion dimension can correspond to particular implant stems, such as series of a particular model of stems.

In still another arrangement, the stem attachment structure can be removably insertable in the joint head and can include one or more series of stem attachment structures, where each stem attachment structure can provide one or more unique dimension relative to the stem attachment structures in the series. The dimension can be one or more of stem attachment length, stem attachment taper and a combination thereof or any other relevant dimension.

Also in accordance with the inventive aspects, a method of performing joint replacement surgery is provided. The method can include the steps of installing an intraoperative joint head having a force sensor housed by the joint head and a stem attachment structure, where the stem attachment structure can be removably attachable to a stem, measuring joint forces, such as the soft tissue tension, and adjusting an implant parameter based on the measured joint forces. The method can also include the step of applying a force to the joint and applying a motion to the joint, such as articulating an appendage throughout its full range of motion.

In one embodiment, the implant parameter can be one or more of a stem dimension, a joint head dimension, stem attachment structure dimension, cavity taper, trunion dimension and a combination thereof or any other suitable dimension. The method can further include the step of implanting an implant based on the measured joint forces. Also, the method can include the steps of obtaining anatomical measurements and selecting one or more of a stem dimension, a joint head dimension, a stem attachment structure dimension, and a combination thereof based on one or more of the measured joint forces, the anatomical measurements, or a combination thereof. Still further, the method can include the steps of obtaining anatomical measurements and implanting an implant based on one or more of the measured joint forces, the anatomical measurements, or a combination thereof or any other suitable measurement.

Also in accordance with the inventive arrangements, a surgical system for measuring joint forces during surgery is provided. The system can include an intraoperative joint head having a stem attachment structure where the stem attachment structure can be removably attachable to a stem, and a force sensor housed by the joint head for measuring in vivo forces during surgery. The in vivo forces can be generated from one or more of tension provided by soft tissue, load application during surgery, limb movement during surgery, and a combination thereof. The system can also include an anatomical tracking system for tracking movements of body parts where the system can be in communication with the force sensor. Further, the system can include a processor in communication with the anatomical tracking system and the force sensor, where the processor can be programmed to provide calculations from one or more of in vivo joint reaction forces, in vivo joint vectors and combination thereof.

BRIEF DESCRIPTION OF THE DRAWINGS

There are shown in the drawings embodiments which are presently preferred, it being understood, however, that the invention is not limited to the precise arrangements and instrumentalities shown.

FIG. 5 is a perspective view of one embodiment in accordance with the inventive arrangements.

DETAILED DESCRIPTION OF THE PREFERRED EMBODIMENTS

The present invention provides an intraoperative device, kit, method and system for measuring joint forces experienced by implants so that surgeons can quantify needed adjustments for implants and prosthetics. In contrast to the prior art, with the device, kit, method and system, surgeons can measure joint forces, such as soft tissue tension, intraoperatively, make adjustments based on measurements instead of subjective observation, and provide optimal implant placement and size. Importantly, the intraoperative device not only allows the surgeon to obtain quantitative soft tissue tension measurements that are unique to the patient due to unique anatomical size and shape, the detachable arrangement of the device allows the surgeon to obtain soft tissue tension measurements for a variety of different implant sizes and arrangements. Such a removably attachable device can allow the surgeon to select the optimal implant size and arrangement based on quantitative measurements without subjecting the patient to the potentially harmful implanting and removing of multiple test components that are integrated and do not provide attached and detachable components.

As used herein, intraoperative refers to components constructed and arranged for surgery and in contrast to those components constructed and arranged to be more permanent in nature as a component used for testing in the lab. Intraoperative also refers to procedures occurring during surgery.

As also used herein, soft tissue tension or tension provided by soft tissue refers to a force or forces at, or in the vicinity of a joint and generated by one or more soft tissues. Soft tissues can be any non-skeletal tissue, such as muscles, tendons, ligaments, and fascia. By way of example, the tension provided by the attachment of the abductor muscle to the femur and to the pelvic bone is a soft tissue tension. The force of the tension is a function of, among other factors, the distance between the two points of attachment. The placement and size of an implant can vary the distance between attachment points, and thus vary the soft tissue tension. The soft tissue tension is one of the many forces experienced by a joint and measurable intraoperatively by the device described herein.

Figure 1:
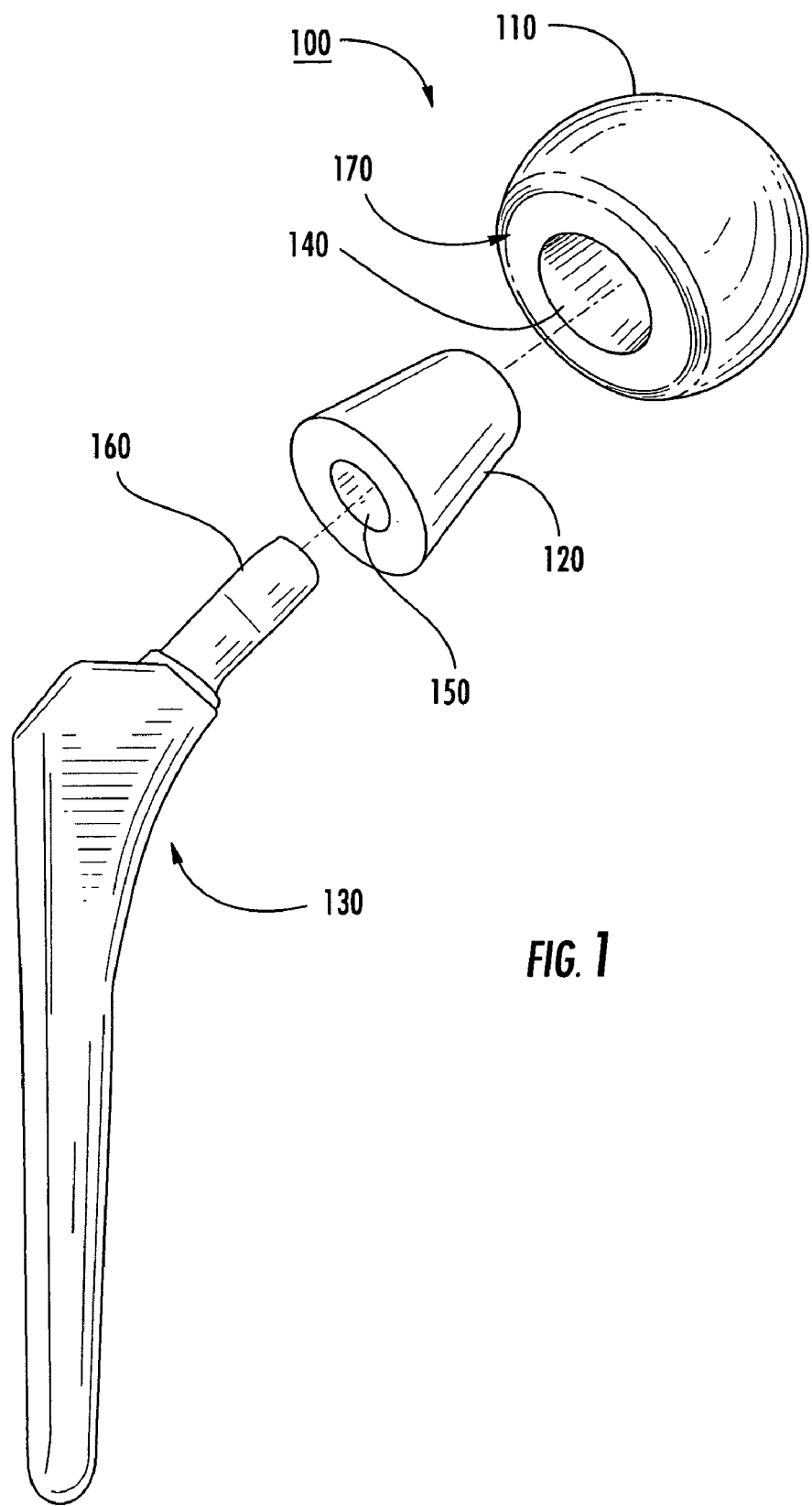
FIG. 1 is an exploded perspective view of an embodiment in accordance with the inventive aspects.

There is shown in FIG. 1 a device 100 with an intraoperative joint head 110, a stem attachment structure 120, and a stem 130. The joint head 110 provides a cavity 140 for insertion of the stem attachment structure 120 and the stem attachment structure 120 provides a recess 150 for insertion of trunion 160. The force sensor (not shown) can be housed within the joint head 110 or can be housed in the stem attachment structure 120.

The joint head 110 can be shaped to mimic the shape of the anatomy to be replaced, and thus, is not limited to any particular anatomical shape or body part. In one example, the joint head 110 can be at least partially spherically shaped with a non-spherically shaped end 170 arranged for insertion of the stem attachment structure 120 and attachment to the stem 130. In such an example, the joint head 110 can be shaped as a femoral head. In another example, the joint head 110 can be shaped as a humeral head. The cavity 140 can provide a tapered shape to allow for insertion of a variety of different sized and shaped stem attachment structures 120. Such a shape advantageously provides for flexibility in testing a variety of different prosthetic arrangements without the need for multiple parts as a joint head 110 can be paired with variously shaped attachment structures 120 that adjust the joint offset, such as the femoral offset. Also, the tapered shape allows for insertion of the stem attachment structure 120 so that a snug fit is formed. The snug fit securely, yet removably, attaches the stem attachment structure 120 to the joint head 110 so that the components can be moved throughout a range of motion and forces applied to the components without the components detaching. Of course, a tapered shape is not required as the cavity 140 can have any shape, such as a cylinder that does not taper. Further, it should be noted that the joint head 110 can be constructed and arranged to correspond to a trunion dimension to ensure compatibility with stem having a particular trunion shape and size.

The stem attachment structure 120 can be shaped to insert into the joint head 110, and like the cavity 140, the stem attachment structure 120 can have a tapered shape. The tapered shape of the attachment structure 120 can correspond to the tapered shape of the cavity 140 so that the two components can be securely attached without the need for any reinforcement, such as an adhesive or screw or bolt. However, such reinforcements may be used. Further, the stem attachment structure 120 and the cavity 140 may be correspondingly threaded such that the components securely screw together. Additionally, although the stem attachment structure 120 is shown with a generally frusto-conical shape, the attachment structure 120 can have any suitable shape.

The stem 130 can be any stem suitable as an intraoperative trial component or as an implant. The trunion 160 of stem 130 can be of a suitable size for insertion in the recess 150 of the stem attachment structure 120. Also, although the length of the trunion 160 can be any suitable length, the length of the trunion 160 can influence the offset from the joint center, such as the femoral offset. Accordingly, the dimensions of the stem 130 and trunion 160 are not limited and can be customized to the anatomy of the patient.

The intraoperative joint head 110, the stem attachment structure 120 and the stem 130 can be constructed of any suitable material, such as titanium, stainless steel, cobalt-chrome alloy, a polymer, or a ceramic. Each component can be constructed of any suitable material that can withstand medical industry standard sterilization processes. A non-exhaustive list of such materials include surgical steels which do not degrade from exposure to high temperatures associated with sterilization by steam and plastics that do not degrade under high energy radiation sterilization. It should be noted that the invention is not limited in this regard as the components can be constructed of other materials that cannot withstand medical industry standard sterilization processes. Thus, the components can be designed for single patient use and can be considered as disposable.

Figure 2:
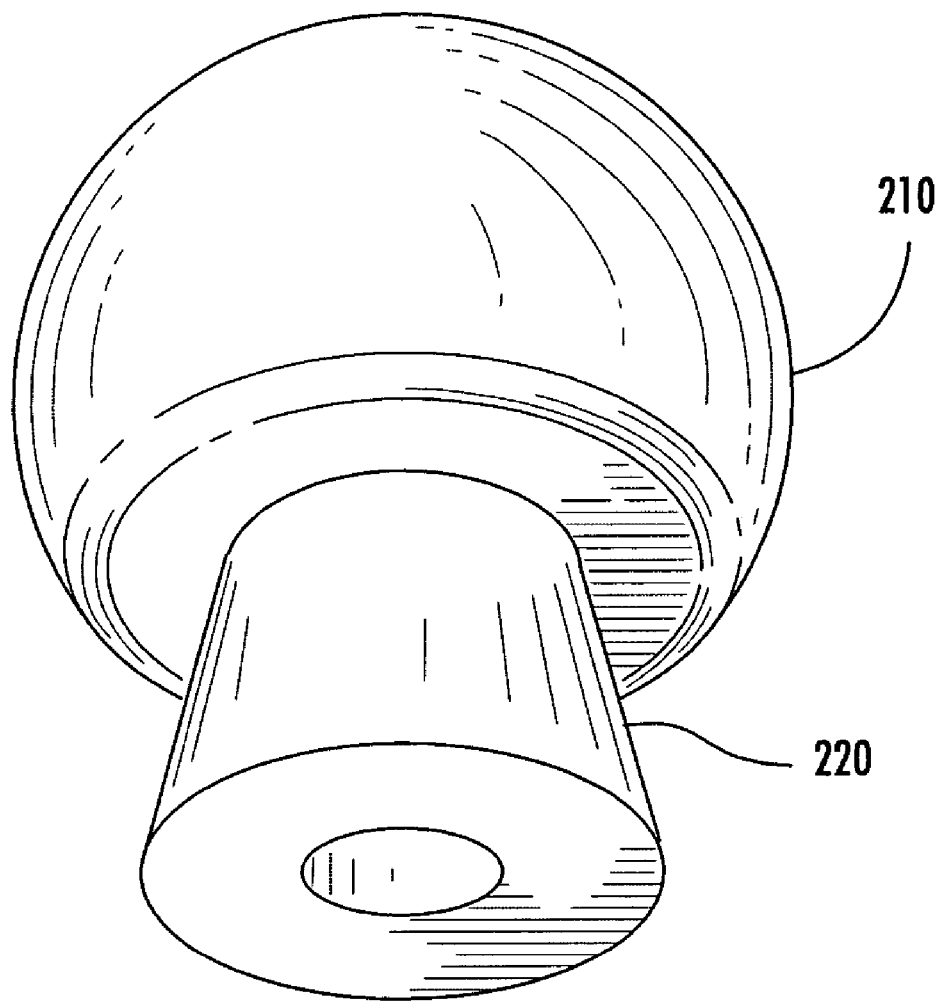
FIG. 2 is a perspective view of one embodiment in accordance with the inventive aspects.

FIG. 2 illustrates one embodiment of the intraoperative device 200 where the stem attachment structure 220 is attached to the joint head 210. In this embodiment, attached components can be considered integrated and one component not designed to be separated. In this embodiment, the component can be attached directly to the stem (not shown).

Figure 3:
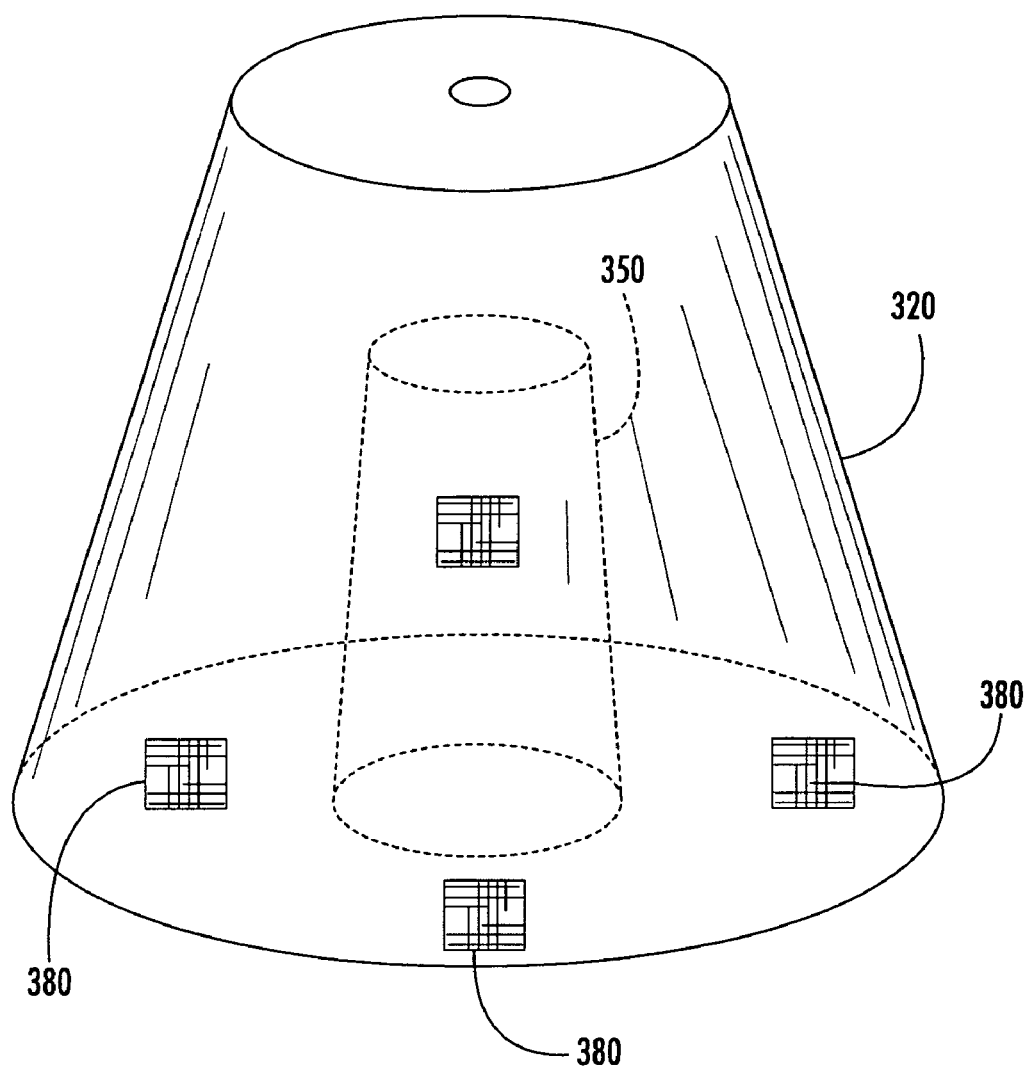
FIG. 3 is a perspective view of one embodiment with internal portions shown with dotted lines in accordance with one embodiment of the inventive aspects.

FIG. 3 illustrates one embodiment of stem attachment structure 320 with a force sensor 380. As shown, the stem attachment structure 320 can house the force sensor 380. The force sensor 380 can be located in a generally central position that lies along an axis of the stem (not shown) that inserts in the recess 350. Such a placement advantageously creates an instrumented beam, from which endpoint force conditions can easily be determined. However, it should be noted that the force sensor, or even multiple force sensors, can be positioned offset from the axis of the stem, as shown. Accordingly, the placement of force sensor 380, or the combination of multiple force sensor 380 is not limited.

The force sensor 380 can be a strain gauge for measuring forces experienced by the patient at the relevant joint. The strain gauge can include a flexible backing that supports a metallic foil etched onto the backing. As the backing is deformed, the foil pattern is deformed, causing its electrical resistance to change. The strain gauge also can include a semiconductor material with an appropriate electrical response to mechanical deformation. Additionally, the force sensor 380 can be configured to measure a uni-axial strain, or can be configured to measure multi-axial strains. For instance, the force sensor 380 can be a multi-axial strain gauge.

The force sensor 380 can be in communication with a circuit, such as a wheatstone bridge circuit, to calculate the force. The force sensor 380 can communicate the results via wired connections (not shown) or via any suitable wireless communication protocol, such as radio frequency. In one example of wireless communications, the force sensor 380 can include a microelectromechanical systems (MEMS) strain gauge with wireless communications circuitry. Other wireless communication circuitry can also be provided. As will be discussed further, the force sensor 380 can be in communication with a communications bus for reading individual measurements and for combining with other measurements or patient data.

Figure 4A:
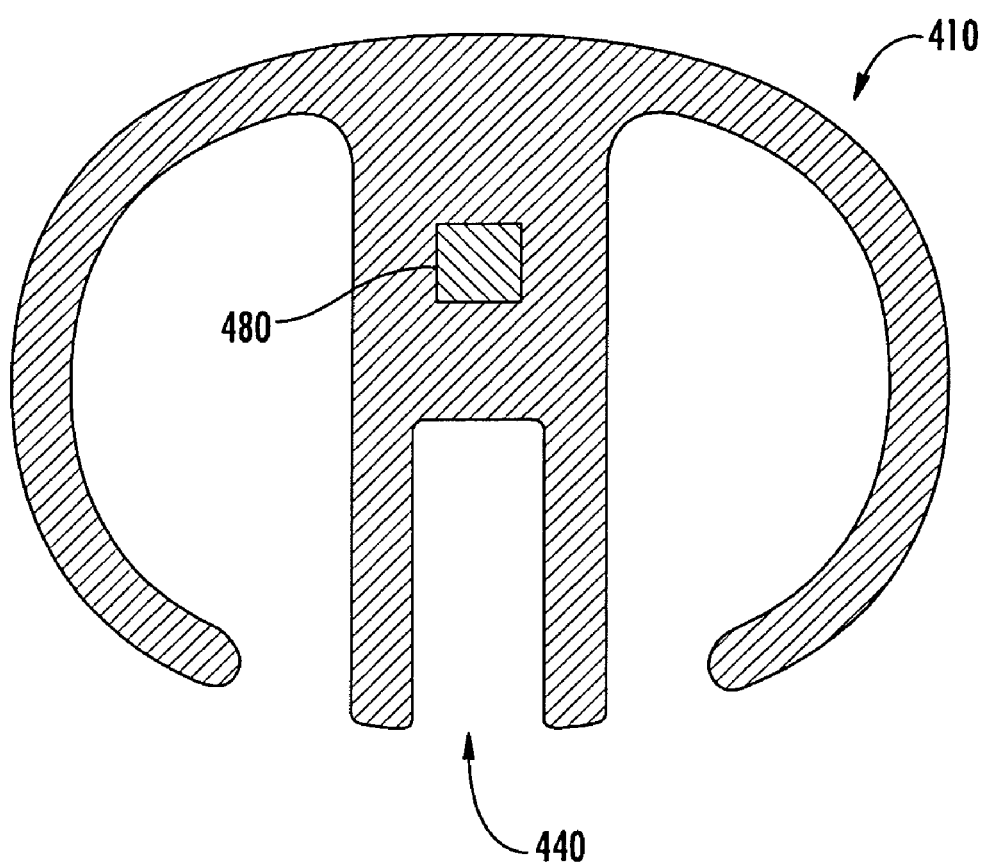
FIG. 4A is a cross-sectional view of one arrangement in accordance with the inventive arrangements.
Figure 4B:
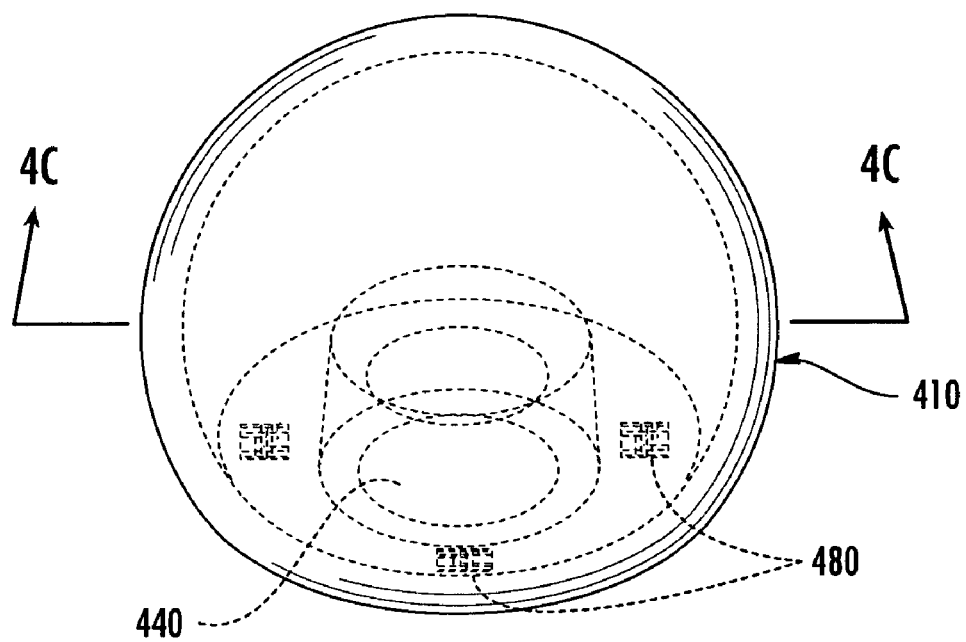
FIG. 4B is a perspective view of one embodiment with internal portions shown with dotted lines in accordance with one embodiment of the inventive aspects.
Figure 4C:
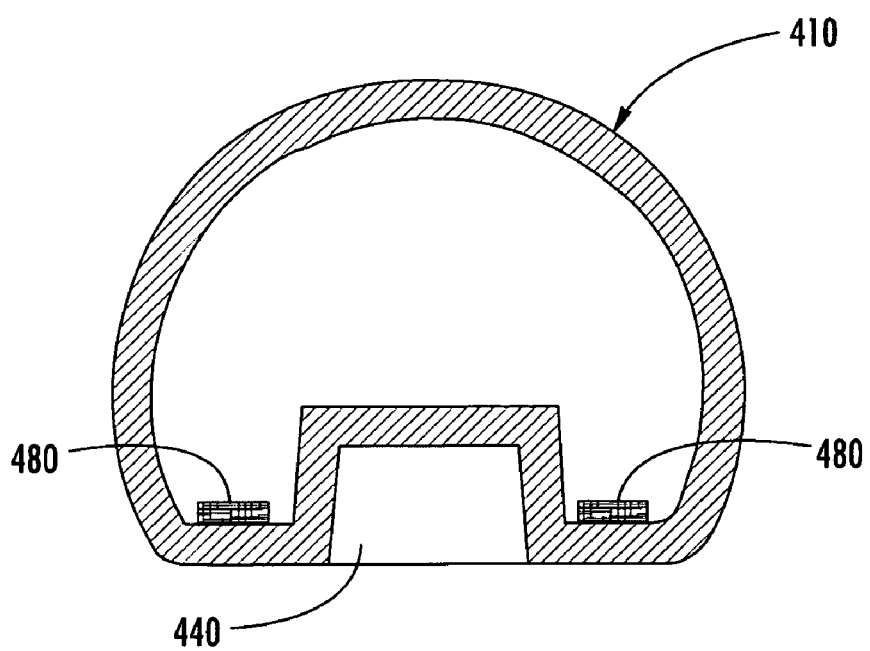
FIG. 4C is a cross-sectional view of the embodiment shown in FIG. 4B taken along line 4-4.

FIGS. 4A-4C illustrate another embodiment of the inventive arrangement, where the force sensors 480 are housed in the joint head 410. FIG. 4A is a cross sectional view of a joint head 410 where the force sensor 480 is located along a generally central position that lies along an axis of the trunion of the stem (not shown) that inserts in the recess 440. The central location position provides the advantage of instrumented beam, from which endpoint force conditions can easily be determined. In this embodiment, the force sensor 480 can be a multi-axial strain gauge for measuring forces along more than one axis. Alternatively, if desired, the force sensor 480 can be configured to measure the force along one axis.

FIG. 4B illustrates a joint head 410 with the force sensors 480 located offset from an axis of the stem (not shown) and FIG. 4C is a cross-sectional view of joint head 410 shown in FIG. 4B and taken along line 4-4. The force sensors 480 are evenly distributed around the periphery of the cavity 440 to assist in determining the component forces of the resultant joint vector. In this embodiment, the force sensors 480 can be uni-axial strain gauges to measure forces along an individual component axis. In such an arrangement, the measurements can be combined to determine joint reaction forces, a joint reaction vector, and joint force or load moments to help determine the summation of the load on the joint. For instance, the measurements can be combined to calculate the summation of soft tissue tension on the joint. However, it should also be noted that the one or more of the force sensor 480 can be multi-axial strain gauges that can provide multiple forces in component form. Multi-axial strain gauges advantageously can provide component forces measured where intraoperative conditions are such that aligning the force sensor 480 along principal component axis is prohibitively complicated and difficult. Additionally, the force sensors 480 can be distributed in any fashion desired and are not limited to a uniform distribution around the periphery of the joint head 410.

There is shown in FIG. 5 a kit 500 for assisting joint replacement procedures. The kit can include trial joint heads 510, stem attachment structure 520, and intraoperative joint head tool 530a and/or 530b. The joint heads 510, stem attachment structure 520, and tools 530a and 530b can be provided as one or more series of components where each component has at least one unique dimension so that one kit can be used for patients with a wide range of anatomical features, size and shape. Joint heads 510 with integrated stem attachment structure 520 are also possible for inclusion in kit 500. The kit 500 provides a plurality of components to modify limb length, joint offset, neck length, neck anteversion so that the effect of these changes can be quantitatively measured to ensure optimal joint forces, such as the tension provided by soft tissue.

Tool 530a is an assembly tool for forcing together a joint head 510 and a stem attachment structure 520 and can compress these components in the direct shown by the arrows. Tool 530b can be a disassembly tool with a U-shaped structure 540 for engaging a stem attachment structure 520 or a stem and joint head engagement structure 550 for engaging a joint head 510. In operation, joint head engagement structure 550 and attachment structure 520 move in the direction shown by the arrows to separate joint head 510 from a stem attachment structure 520 or directly from a trunion or stem. The tools 530a and 530b can be any tool suitable for assembling or dissembling the joint head with a stem attachment structure and/or a stem. Other tools, such as a mallet, can be provided.

The kit 500 can also include one or more series of trial joint heads 510, where each joint head 510 includes one or more unique dimensions. The joint heads 510 can include one or more unique dimensions of the joint head diameter (hd), joint head cavity depth (cd), taper (t), trunion dimension (td) and any other desirable dimension. The taper (t) refers to the increase or decrease of joint head diameter (hd) along the length of the joint head cavity depth (cd). The trunion dimension (td) refers to a combination of one or more of the cavity dimensions that correspond to a correspondingly shaped trunion of an implant. For example, the kit can provide a series of joint heads of increasing joint head diameter (hd) so that the surgeon can obtain measurements using multiple joint heads to determine the optimal configuration and positioning. Multiple combinations of joint head dimensions can be provided. A non-exhaustive exemplary list of joint head diameter (hd) dimensions include 22 mm, 26 mm, 28 mm, and 32 mm. Other dimensions are possible.

Likewise, the kit 500 can include one or more series of stem attachment structures 520, where each stem attachment structure 520 provides a unique dimension. The stem attachment structures 520 can include one or more stem attachment length (al) and stem attachment taper (at), which represents the increase or decrease in attachment structure 520 width along the stem attachment length (al), or can be considered the slope of the side of attachment structure 520. The unique dimension can be any other desirable dimension or combination thereof.

As noted above, the kit 500 with multiple components, in various combinations of unique dimensions, can provide the surgeon with a complete set of components for not only measuring the joint forces, but also testing different sized components and positioning in vivo. Other items can also be provided with the kit 500, such as other tools or components.

Figure 6:
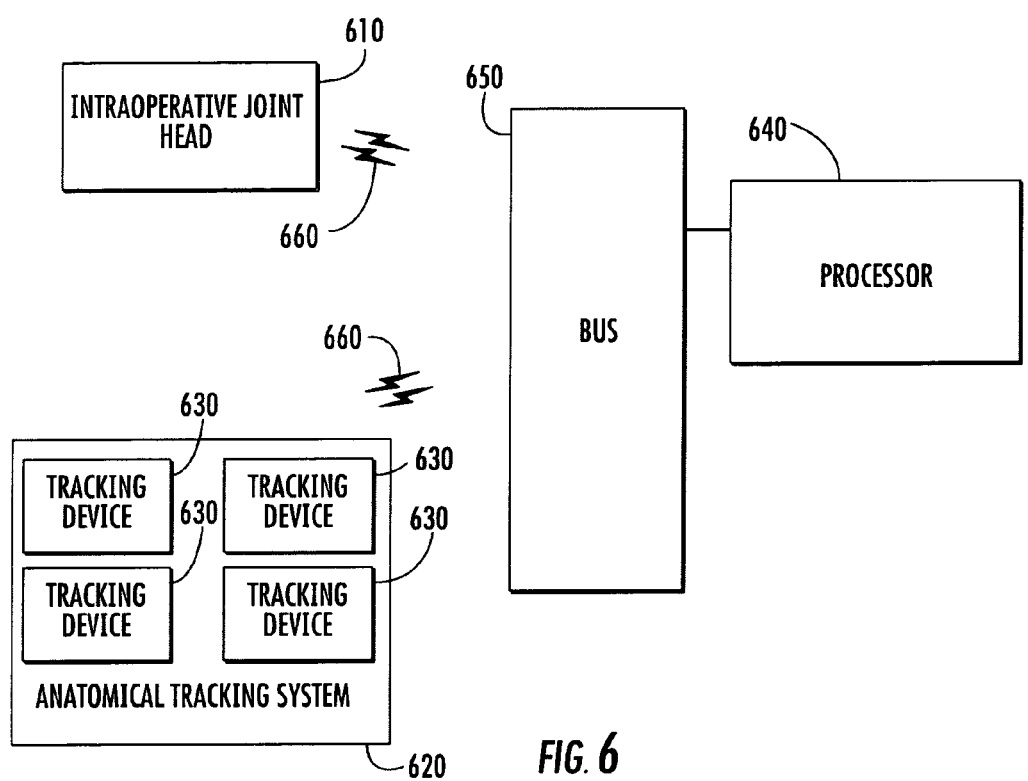
FIG. 6 is a schematic view of one arrangement of a system in accordance with the inventive arrangements.

The components can also be used in cooperation with an anatomical tracking system as shown in FIG. 6. FIG. 6 illustrates system 600 for measuring joint forces during surgery and includes a joint head measuring device 610, tracking system 620 with trackers 630, such as an optical tracking system with optical trackers, and a processor 640, such as any suitable computing system for providing calculations. The processor 640 can be provided with suitable software for rendering computer animations of the patient's limbs. On example of such software is the VectorVision® software system provided by BrainLab USA. The components of system 600 can communicate over wired or wireless communications of link 660 via communications bus 650. The system 600 can provide the surgeon with a computer assisted surgical advantage by rendering the patient's anatomy, and joint forces experienced under various loads.

The optical tracking system 620 can be used with the optical trackers 630 placed at reference points along the patient's body. The optical trackers 630 can identify a displacement during movement, which allows the processor 640 to render images of the patient's anatomy in various configurations. Pre-operative images, obtained via any suitable method such as a CT scan, can be combined such that renderings of patient's limbs are based on the patient data. Nevertheless, it should be noted that such images are not necessary as computer models can be generated from other measurements, such a limb length and width. Further, it should also be noted that system 600 can include non-optical tracking devices such as electromagnetic, acoustic, and/or mechanical linkage based devices.

In addition to providing a rendering of the patient's limb at various configurations, the processor 640 can provide a graphical display of the forces measured by the joint head measuring device 610. The display can include individual forces, individual vectors, joint reaction forces, and joint reaction vectors. Providing real-time measurements may alert the surgeon to forces experienced by a joint that may not be discemable to the naked eye.

Thus, with system 600, the surgeon can test a variety of different joint head measuring devices, stems, and stem attachment structures to quantitatively capture the effect of altering implant dimensions. Reviewing a display of the joint reaction vector obtained by an intraoperative joint head measuring in vivo forces, such as the soft tissue tension experienced at a joint. With system 600, the surgeon can provide optimal implant size, shape, arrangement, and orientation unmatched by the manual testing and best judgments used in the past.

Figure 7:
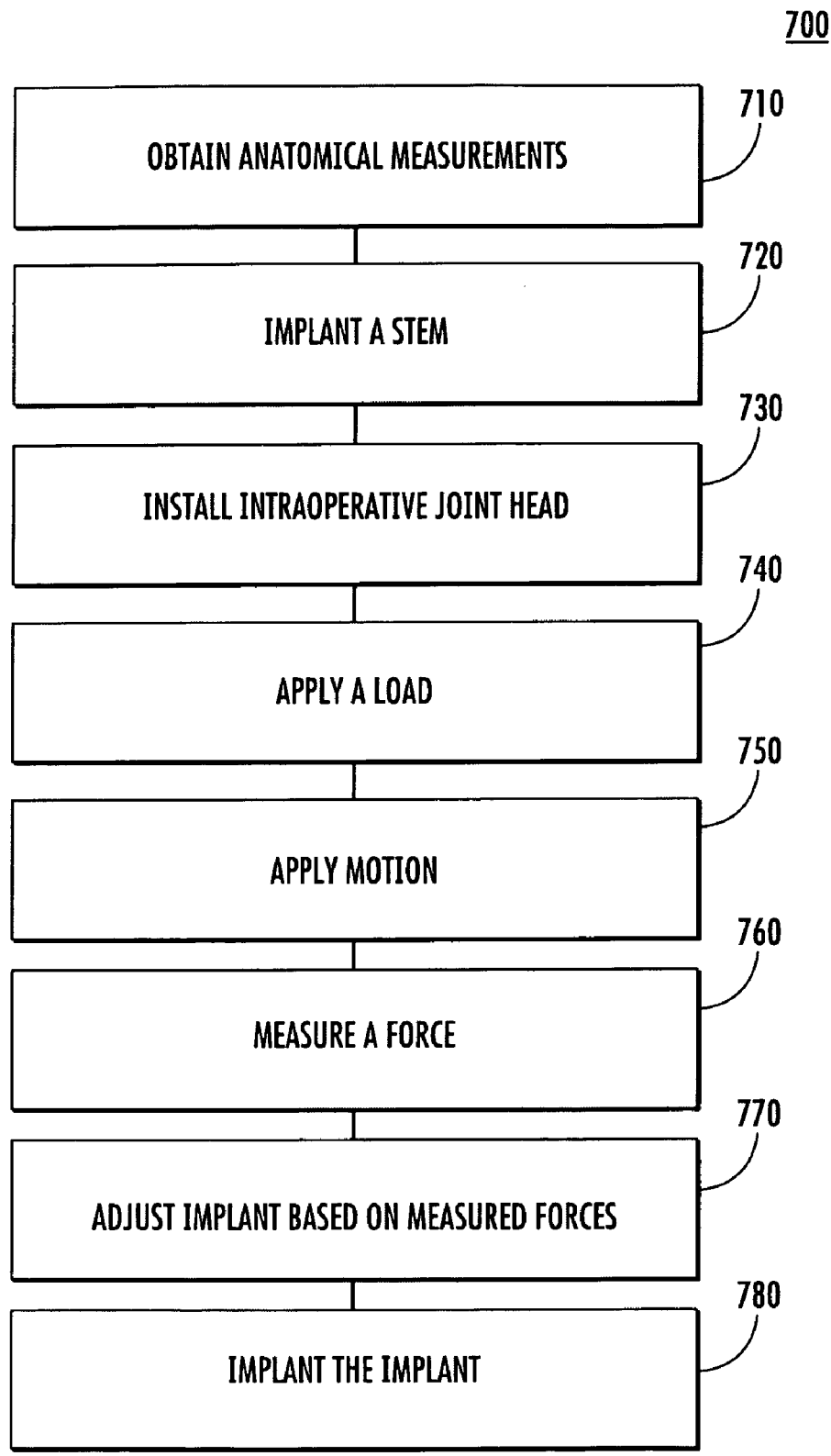
FIG. 7 is a flow chart of a method in accordance with the inventive arrangements.

FIG. 7 provides a flow chart of one arrangement of a method of performing joint replacement surgery. Although the method 700 is discussed with reference to the components discussed herein, it should be noted that the method can be practiced without limitation to particular components. Also, steps of method 700 can incur in any order desired.

In operation, anatomical measurements, such as height, weight, various bone lengths, and the like, of the patient can be obtained in step 710. These measurements include measurements of the joint to be operated on, attached limbs, and any other anatomical measurement that may be helpful. For instance, it may be beneficial to obtain the measurements of a healthy joint, in order to conform the implant to those measurements. Also, measurements such as the patient's weight may play a significant role in determining the appropriate implant size, positioning, orientation and arrangement.

In step 720, a stem is implanted. The stem can be either an intraoperative stem used only during the surgery, or can be the implant that will be used after surgery. The stem can be implanted in a commonly accepted fashion, such with or without bone cement. In a cementless system, the implant stem can be fitted to the bone with a screw or by press-fit.

In step 730, an intraoperative joint head can be installed. The intraoperative joint head can include stem attachment structure, either integrated with the joint head or as a separate component. Various combinations of uniquely dimensioned joint heads and/or attachment structures can be used to vary the joint positioning, orientation and arrangement. Through the use of joint heads with unique dimensions of joint head cavity depth and joint head radius length, the femoral offset can be altered incrementally.

In step 740, a load can be applied. The load can be applied by subjecting the joint to a force, such a force to mimic the patient's weight. Other loads can also be applied where desired. Nevertheless, it should be noted that the soft tissue tension provided without any movement can be the applied load.

In step 750, a motion can be applied. For instance, a patient's limb can be moved throughout its entire range of motion. As one example, the shuck test, which is used to determine soft tissue tension in a distal direction, can be used to apply loads and to obtain in vivo force measurements.

In step 760, forces can be measured by the intraoperative joint head measuring device. The forces can be measured as a joint reaction force, a joint reaction vector, or as their component forces and vectors. It should be noted that the measured force can be a measurement of the tension provided by soft tissue. If available, the joint head measuring device can be used in combination with pre-operative images or an anatomical tracking system to display a rendering of the forces and/or vectors. In a surgical setting, the renderings can be displayed to a surgeon in real-time for the surgeon to base alterations on the forces measured.

In step 770, the implant can be adjusted based on the measured forces. The implant can include the stem, the attachment structure, the joint head, or any other component used for implantation. The implants can be adjusted or replaced in response to the force measurements obtained to achieve an optimal joint reaction force and/or joint reaction vector. In other arrangements, the implants can be adjusted to obtain an optimal soft tissue tension. It should be noted that various combinations of implants can be tested to measure joint forces so that the optimal size, configuration, position, orientation, and arrangement can be achieved. Further, it should be noted a plurality of the steps of method 700 can be repeated to obtain the optimal arrangement and implant size.

In step 780, the implant can be implanted into the patient. The implant can include the components used during the testing and force measurement, or can be implants based on those measurements and tests. Thus, it should be noted that in some instances, it may be beneficial to implant the intraoperative joint head for use by the patient after surgery. In some situations, it may be beneficial to obtain measurements well into the future after surgery is completed and the patient has had time to recover.

While the preferred embodiments of the invention have been illustrated and described, it will be clear that the invention is not so limited. Numerous modifications, changes, variations, substitutions and equivalents will occur to those skilled in the art without departing from the spirit and scope of the present invention as described in the claims.

What is claimed is:

1. A surgical device for joint replacement surgery, comprising:
   an intraoperative joint head having a cavity for accepting the insertion of a stem attachment structure;
   a stem attachment structure being removably attachable to a stem and removably insertable in the joint head cavity;
   a plurality of force sensors disposed within the joint head for measuring in vivo forces during surgery;
   wherein the force sensors are placed at the periphery of the joint head cavity and the distance between adjacent force sensors is uniform, and at least one force sensors is located coaxial with a longitudinal axis of the stem such that the plurality of force sensors measure joint component forces to determine the resultant joint vector; and
   wherein the in vivo forces are generated from the group consisting of tension provided by soft tissue, load application during surgery, limb movement during surgery, and a combination thereof.

2. The device according to claim 1, wherein the plurality of force sensors that are placed at the periphery of the joint head cavity comprise three force sensors, each force sensor being located approximately 90° from an adjacent force sensor.

3. The device according to claim 1, wherein the joint head is at least partially spherically shaped.

4. The device according to claim 3, wherein the joint head is shaped as an anatomical structure from the group consisting of a femoral head, a humeral head, and a combination thereof.

5. The device according to claim 1, wherein the stem is the implant and the joint head is a trial joint head dimensioned as an implant for measuring in vivo forces during surgery.

6. The device according to claim 2, wherein the stem attachment structure includes a recess for receiving insertion of the stem.

7. The device according to claim 1, wherein the force sensor is a strain sensor.

8. A kit for assisting joint replacement procedures, the kit comprising:
   an intraoperative joint head having a cavity for accepting the insertion of a stem attachment structure;
   a stem attachment structure being removably attachable to a stem and removably insertable in the joint head cavity;
   a plurality of force sensors disposed within the joint head for measuring in vivo forces during surgery;
   wherein the force sensors are placed at the periphery of the joint head cavity and the distance between adjacent force sensors is uniform, and at least one force sensors is located coaxial with a longitudinal axis of the stem such that the plurality of force sensors measure joint component forces to determine the resultant joint vector;

wherein the in vivo forces are generated from the group consisting of tension provided by soft tissue, load application during surgery, limb movement during surgery, and a combination thereof; and an intraoperative joint head tool.

9. The kit according to claim 8, wherein the joint head includes at least one series of joint heads, each joint head providing at least one unique dimension relative to the joint heads in the series, the dimension selected from the group consisting of joint head radius, joint head cavity depth, cavity taper, trunion dimension and a combination thereof.

10. The kit according to claim 8, wherein the stem attachment structure is removably insertable in the joint head and includes at least one series of stem attachment structures, each stem attachment structure providing at least one unique dimension relative to the stem attachment structures in the series, the dimension selected from the group consisting of stem attachment length, stem attachment taper and a combination thereof.

11. The kit according to claim 8, wherein the intraoperative joint head tool includes a tool selected from the group consisting of an assembly tool and a disassembly tool.

12. A method of performing joint replacement surgery, comprising the steps of:

installing an intraoperative joint head having a cavity for accepting the insertion of a stem attachment structure; a stem attachment structure being removably attachable to a stem and removably insertable in the joint head cavity; a plurality of force sensors disposed within the joint head for measuring in vivo forces during surgery; wherein the force sensors are placed at the periphery of the joint head cavity and the distance between adjacent force sensors is uniform, and at least one force sensor is located coaxial with a longitudinal axis of the stem such that the plurality of force sensors measure joint component forces to determine the resultant joint vector; and wherein the in vivo forces are generated from the group consisting of tension provided by soft tissue, load application during surgery, limb movement during surgery, and a combination thereof;

measuring joint forces;

determining the resultant joint force vector; and adjusting an implant parameter based on the measured joint forces.

13. The method according to claim 12, further comprising the step of applying a force to the joint.

14. The method according to claim 12, further comprising the step of applying a motion to the joint.

15. The method according to claim 12, wherein the implant parameter is selected from the group consisting of a stem dimension, a joint head dimension, stem attachment structure dimension, cavity taper, trunion dimension and a combination thereof.

16. The method according to claim 12, further comprising the step of implanting an implant based on the measured joint forces.

17. The method according to claim 12, further comprising the steps of obtaining anatomical measurements; and selecting a stem dimension, a joint head dimension, stem attachment structure dimension, and a combination thereof based on the measured joint forces, the anatomical measurements and a combination thereof.

18. The method according to claim 12, further comprising the steps of obtaining anatomical measurements; and implanting an implant based on the measured joint forces, the anatomical measurements and a combination thereof.

19. A surgical system for measuring joint forces during surgery, comprising:

an intraoperative joint head having a cavity for accepting the insertion of a stem attachment structure; a stem attachment structure being removably attachable to a stem and removably insertable in the joint head cavity; a plurality of force sensors disposed within the joint head for measuring in vivo forces during surgery; wherein the force sensors are placed at the periphery of the joint head cavity and the distance between adjacent force sensors is uniform, and at least one force sensor is located coaxial with a longitudinal axis of the stem such that the plurality of force sensors measure joint component forces to determine the resultant joint vector; and wherein the in vivo forces are generated from the group consisting of tension provided by soft tissue, load application during surgery, limb movement during surgery, and a combination thereof;

an anatomical tracking system for tracking movements of body parts, the system in communication with the force sensor; and a processor in communication with the anatomical tracking system and the force sensor, the processor programmed to provide calculations selected from the group consisting of in vivo joint reaction forces and in vivo joint vectors.

* * * * *